United States Patent [19]

Poirier

[11] 4,104,005
[45] Aug. 1, 1978

[54] PNEUMATIC BLADDER PUMP HAVING STIFFNESS SYMMETRY

[75] Inventor: Victor L. Poirier, Chelmsford, Mass.

[73] Assignee: Thermo Electron Corporation, Waltham, Mass.

[21] Appl. No.: 647,842

[22] Filed: Jan. 9, 1976

[51] Int. Cl.² .................. F04B 43/08; F04B 43/10; F04B 45/06
[52] U.S. Cl. .................. 417/394; 417/478; 285/281
[58] Field of Search ......... 417/383, 384, 385, 478, 417/394; 128/DIG. 3; 222/95; 220/63 R; 285/DIG. 6, 281; 60/259, 39.48

[56] References Cited

U.S. PATENT DOCUMENTS

| 723,042 | 3/1903 | Schwerin | 417/478 |
|---|---|---|---|
| 1,976,415 | 10/1934 | Scott | 417/478 |
| 3,062,153 | 11/1962 | Losey | 417/478 |
| 3,218,979 | 11/1965 | Baldwin | 417/478 |
| 3,286,878 | 11/1966 | Schadt et al. | 60/39.48 |
| 3,550,162 | 12/1970 | Huffman et al. | 417/394 |
| 3,814,547 | 6/1974 | Kitralakis et al. | 417/478 |

FOREIGN PATENT DOCUMENTS 800,805  11/1950  Fed. Rep. of Germany ........... 417/478

OTHER PUBLICATIONS

Marks' Mechanical Engineers' Handbook, Baumeister (editor), McGraw-Hill Book Co. Inc., 1958, Chp. 5, pp. 63–65.

Primary Examiner—Carlton R. Croyle
Assistant Examiner—Thomas I. Ross
Attorney, Agent, or Firm—James L. Neal; David W. Gomes

[57] ABSTRACT

A compact blood pump includes a flexible bladder mounted within a rigid metal housing. Pneumatic pulses between the bladder and the housing produce pumping action in association with appropriate inlet and outlet valves. The bladder is configured to provide a stiffness characteristic which produces a recurring three lobe collapse pattern during pumping operation. Inlet and outlet passages to the bladder are associated with detachable seal rotatable fluid conduits in fluid-tight relationship to the bladder. The conduits are attachable and rotatable without transmitting torque to the flexible bladder.

8 Claims, 3 Drawing Figures

PNEUMATIC BLADDER PUMP HAVING STIFFNESS SYMMETRY

The invention described herein was made in the course of or under a contract with the U.S. Department of Health, Education and Welfare.

BACKGROUND OF THE INVENTION

Substantial efforts to develop and perfect artificial blood pumps have spanned approximately 10 years. Research has been conducted both in the area of heart assist devices and total replacement units. One prominent design involves a flexible bladder enclosed in a metal alloy housing. Gas is injected between the bladder and the housing to cause the bladder to eject its contents through a one-way outlet valve. Release of this gas allows the bladder to expand and fill through a one-way inlet valve. The inside of the bladder is flocked with fibers of a blood-compatible polymeric material to promote formation of a stable biological interface between the blood and the bladder. During normal operation, the inside surfaces of the pump bladder should not be permitted to contact each other. Such contact interferes with the flocked fiber and the biological interface on the bladder surface.

Accordingly, it is an object of the present invention to provide a blood pump in which the inside surfaces of the bladder do not contact each other.

Another object of the present invention is to maximize the volumetric efficiency of the blood pump so as to minimize the overall pump size.

Another object of the present invention is to provide for adjustability of the inlet and outlet conduits of the pump both before and after connection so as to optimize pump performance and avoid interference with a patient's vital organs.

A further object of the present invention is to provide a compact structure arranged so that external shape and surface characteristics will not interfere with a patient's vital organs.

SUMMARY OF THE INVENTION

A compact blood pump for either external or internal operation is provided. An axis-symmetrical polyeurathane bladder enclosed in a titanium alloy housing has inlet and outlet ports located at the axis ends of the bladder. Outwardly extending flanges are formed around the inlet and outlet ports. Metal end adaptors are mounted in the inlet and outlet blood conduits and are adapted to press the bladder flanges against the housing to form a fluid tight seal. The adaptors are held in place by couplings which connect to the housing. Gas rhythmically injected and released between the bladder and the housing produces the desired pumping action in cooperation with one-way valves located in the outlet and inlet conduits. To prevent contact between the bladder surfaces and to maintain maximum pumping capacity, the bladder is configured to insure a recurring three lobe collapse pattern. Three lobe collapse pattern is further assured by avoiding application of torque to the bladder during or subsequent to assembly. This is achieved by Teflon washers installed between the adaptors and the housing couplings and between the adaptors and the bladder flanges.

DETAILED DESCRIPTION OF THE DRAWINGS

Figure 1:
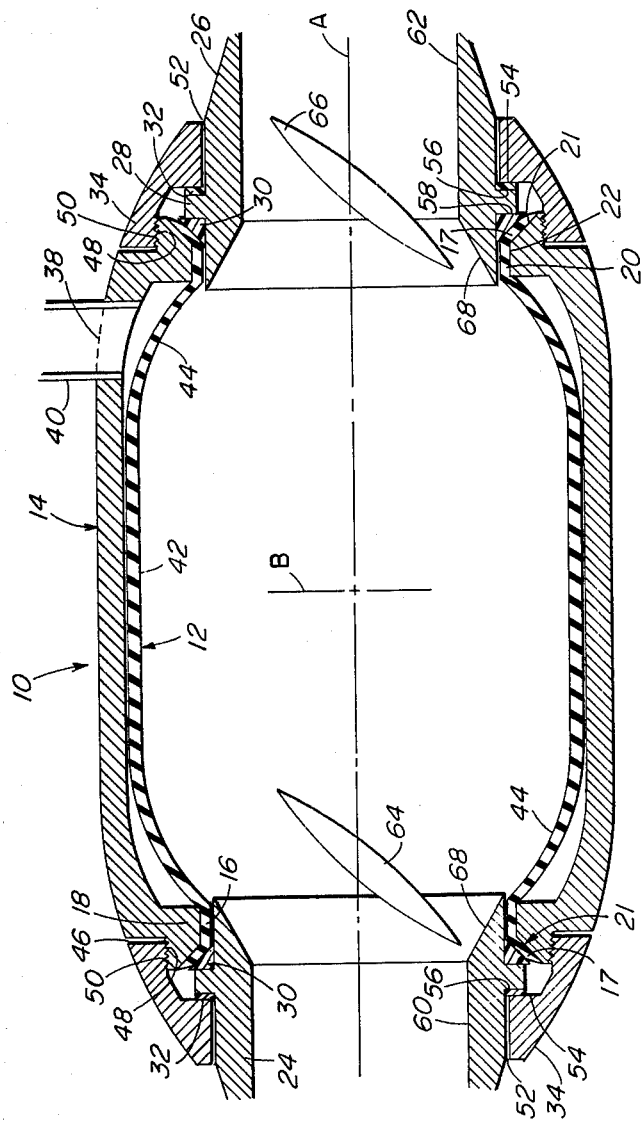
FIG. 1 is a cross-sectional view showing a preferred embodiment of the blood pump of this invention.

Referring to FIG. 1, a blood pump 10 includes a flexible polyeurathane bladder 12 which is axis symmetrical about a longitudinal axis designated A. The bladder is enclosed within a rigid titanium alloy housing 14 having a shape which corresponds generally to the shape of the bladder. The bladder and the housing have mating inlet openings 16 and 18, respectively, and mating outlet openings 20 and 22, respectively. The openings 16 and 20 of the bladder 12 are associated with circumferential lips or flanges 17 defining surfaces 21 which conform with the inlet and outlet openings of the housing 14. The inlet and outlet openings are associated, respectively, with an inlet adaptor 24 and an outlet adaptor 26. These adaptors are identical and each extends from a location interior of the bladder 12, through the associated opening 16 or 20 to a location exterior of the housing 14. Each adaptor is circumscribed by an annular projection 28 which may be associated with seals or rings 30 and 32. The bladder 12, housing 14 and adaptors 24 and 26 are all held in assembled relation by a pair of coupling members 34 which engage the annular projections 28 on the adaptors 24 and 26 and opposite end portions of the housing 14. The housing 14 is further provided with a port 38 for connection to a pneumatic pressure line 40 through which activating pulses are provided to the blood pump as will be subsequently explained.

The embodiment of FIG. 1 and certain of its components and elements will now be discussed in more particular detail so that the purposes and advantages of the invention here described may be more fully understood.

The blood pump 10, symmetrical about axis A, is also symmetrical about a plane B perpendicular to and bisecting the axis A so that it passes through the bladder and the housing mid-way between the inlet and outlet ends thereof. The bladder 12 is constructed with uniform wall thickness from a suitable bio-compatible material. Suitable materials are linear segmented polyeurathane materials marketed under the names Biomer and Lycra. Lycra material is manufactured by and available from E. I. duPont deNemours and Company, Wilmington, Delaware. Biomer material is manufactured and available from Ethicon, Inc., U.S. Route 22, Somerville, New Jersey. Lycra and Biomer are preferred among various bio-compatible materials (e.g. materials compatible with human biological systems) which are currently available because of their superior durability. Materials such as Lycra and Biomer lend themselves well to the dip forming processes and when, as in the embodiment here being described, the bladder is to be of uniform wall thickness, formation of a dipped molding is highly desirable. Orientation of the flange at an angle substantially less than 90°, preferably in the range of 0° to 45°, facilitates the molding process. The interior, blood contacting surfaces of the bladder as well as all other blood contacting surfaces within the pump 10 are coated with a Dacron flock which enables the blood to build up an endothelial layer which adapts these surfaces for prolonged contact with the blood without producing blood damage. This flock is more particularly described in co-pending U.S. Patent Application Ser. No. 602,385, filed Aug. 6, 1975, for "Flocking of Blood Contacting Surfaces of Artificial Implant Devices" in the names of Victor L. Poirier and John T. Keiser. Preferably the inwardly projecting portion of each adaptor 24 or 26 does not contact the surface of the bladder, except that it may be spaced so that it touches the end portions of the flock applied to the inner surface of the bladder.

The above-described bladder 12 has a symmetry of stiffness as well as geometrical symmetry about axis A and plane B. That is, points on the bladder wall which are equidistant from the plane B maintain substantially identical amounts of stiffness or resistance to collapse. This symmetry of stiffness produces a recurring three lobe collapse pattern illustrated in FIG. 2 and more particularly described below.

Figure 2:
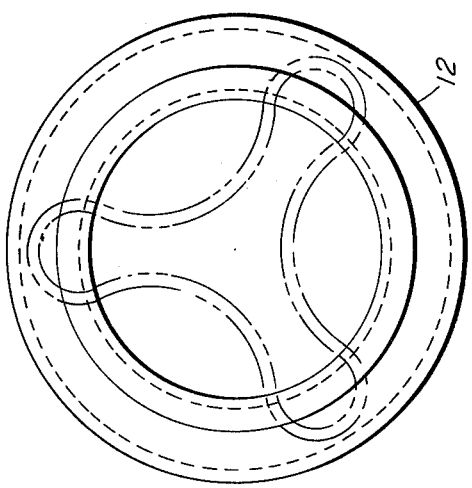
FIG. 2 shows an end view of the embodiment of FIG. 1 with certain parts removed.

As can be appreciated from FIGS. 1 and 2, the bladder includes a central cylindrical portion 42 between zones of gradually decreasing diameter 44 so that the inlet opening 16 and the outlet opening 20 are of smaller diameters than the central portion 42 of the bladder. The flanges 17 extending from adjacent the openings 16 and 20 form the terminal portion of the bladder 12 and serve to provide sealing surfaces between the bladder 12 and the housing 14 and between the bladder and the adaptors 24 and 26. The flanges extend outwardly from the openings 16 and 20 at approximately 45° angles with respect to the axis A. While the angular disposition of 45° is not critical, it is advantageous that the angle be significantly greater than 0° and less than 90° with respect to the axis. An angular disposition greater than 0° facilitates assembly and the formation of an effective seal. Further, flange diverging at less than 90° facilitates initial formation of the bladder 12 by a dip molding process.

The housing 14, adapted to contain the bladder 12, conforms very closely to the bladder shape without actually contacting the bladder wall. The outer surface of the housing presents a continuous and smooth surface without projection or abrupt change in contour which would tend to complicate retention of the pump within a patient's body. Each end of the housing 14 is provided with a recessed area 46 and threads 48. The couplings 34 are internally threaded with threads 50 to mate with threads 48 on the housing 14. The outer surfaces of the couplings are configured to align with that of housing 14 to form a single smooth unbroken outer surface when the pump 10 is fully assembled. The opening 52 in each coupling 34 is sized to receive the associated adaptor 24 or 26 and leave clearance between the adaptor and the coupling in assembled condition. Each opening 52 is surrounded at its inner end by an annular surface 54 facing a corresponding surface 56 on the adaptor projection 28. The opposite side of each adaptor projection 28 forms a surface 58 facing a surface 21 of the bladder 14. An annular ring 32 is positioned between each pair of surfaces 54 and 56. A triangularly sectioned ring 30 is interposed between each surface 58 and the facing surface 21. The triangular sectional configuration of the ring 30 is such that it conforms with the outwardly diverging contour of the associated flange 17 and the corresponding surface 21 of the housing 14.

In assembled condition, the couplings 34 apply axial pressure to the adaptors 24 and 26 through the surface 54 on the couplings. Axial pressure produces fluid tight seals at rings 30, between each bladder flange 17 and its associated adaptor 24 or 26, and also between each flange 17 and its associated openings 18 or 22 in the housing 14. The rings 30 and 32 are formed of a material having a very low coefficient of friction, such as polytetrafluoroethylene, which leaves the adaptors free to rotate relative to the bladder 12 and the associated couplings 34, there being no contact between the bladder and the couplings or the adaptors except through the low-friction rings. The inlet adaptor 24 is provided with inlet conduit 60 and, correspondingly, the outlet adaptor 26 is provided with an outlet conduit 62. Within the conduits 60 and 62 there is provided, respectively, an inlet valve 64 and an outlet valve 66. The valves 64 and 66 are illustrated as conventional tilting disc valves although they may be of other types such as axially movable disc valves or tissue valves such as porcine Xenograph valves. In any event, the valve which is used is most desirably positioned toward the inner portions of the adaptor so that the overall end-to-end length of the blood pump 10 is minimized. The diameter of the inlet and outlet conduits 60 and 62 is substantially smaller than the maximum diameter of the corresponding inlet 16 and outlet 20. The inner end of the adaptors have a surface 68 tapered to form a continuation of the contour of the inner surface of the bladder 12. The surface 68 provides a smooth transition between the conduits 60 and 62 and the bladder 12. This minimizes undesirable turbulence in the blood and generally enhances a desirable flow pattern.

Operation of the apparatus will now be described in connection with FIGS. 1 and 2. The position illustrated in FIG. 1 is that in which the bladder is fully extended and filled with blood. FIG. 2 illustrates an end view of the bladder 12 of FIG. 1, the three lobe collapse pattern being shown in phantom lines.

A timed pneumatic pulse is supplied through the opening 38 to the space within the housing, between the inner surface of the housing wall and the outer surface of the bladder 12. This pulse may be provided in any appropriate manner, as by a system of the type described in co-pending U.S. Patent Application Ser. No. 647,841, filed Jan. 9, 1976 for "Pneumatic Pump Monitor" in the name of David Gernes and U.S. Patent Application Ser. No. 647,679, filed Jan. 9, 1976 for "Blood Pump Stroke Volume Limiter" in the name of Victor L. Poirier. When the pressure surrounding the bladder 12 exceeds the pump outlet pressure, which in operation is the arterial pressure, the bladder collapses in the three lobe pattern shown in FIG. 2. The three lobe collapse maximizes the volumetric displacement from the bladder and is controllable so that the inner surfaces of the bladder do not touch at any point during collapse. Contact between any portion of the inner surfaces of the bladder would disturb the flock and the endothelial layer formed thereon. The valves 64 and 66 operate as one-way check valves so that upon collapse of the bladder 12, the contents of the bladder are expelled through the valve 66, the valve 64 being maintained in closed position. Upon termination of the pneumatic pulse, pressure in the bladder 12 drops, arterial pressure closes valve 66 and pump inlet pressure opens the valve 64 and produces a flow of blood into the bladder. Blood flow into the bladder fills it and extends it to the position shown in FIG. 1 and the cycle is repeated. When the pump is in use as a left ventricular assist device, pump inlet pressure is approximately left ventricular pressure.

The rings 30 and 32 serve important functions in addition to the sealing function noted above. In assembly of the device, which usually takes place during surgery and must occur with care and dispatch, the adaptors having the rings 30 and 28 installed thereon are inserted into the openings in the bladder 12 so that the hypotenuse surfaces of the right-triangular rings 30 abut the diverging inner surfaces 21 of the flange 17 at the terminal ends of the bladder 12. A coupling 34 is then installed over each adaptor and screw-threaded into the housing 14. The rotational motion of the couplings tends to be transmitted through the adaptors to the bladder. If transmission occurs the bladder will twist and will not collapse in an optimum collapse pattern. Slight twisting interferes with the collapse pattern and severe twisting of the bladder may produce premature failure of the device. Because the rings 30 and 32 have a very low coefficient of friction and since the couplings 34 are not in contact with the adaptors 24 and 26 except through the rings 28, the rotational interfaces are effectively lubricated and rotational forces are not transmitted to the bladder 12. After assembly of the blood pump 10 it may be necessary to adjust the rotational position of either or both of the adaptors 24 and 26. The adaptors are connected to blood conduits (not shown) which must be positioned in accordance with the anatomy of the individual patient. Similarly the blood pump 10 must be positioned taking into consideration the angles from which the blood conduits approach. For such reasons, the ability to rotate the adaptors after assembly without either loosening the couplings or providing a torque to the bladder is required. The rings 32 function to permit relative rotation between the couplings 34 and the adaptors 24 and 26 as previously described. Similarly the rings 30 positioned between the adaptors and the bladder 12 permit the adaptors to rotate without undesirable torque being transmitted to the bladder, there being no contact between the adaptors and the bladder except through the rings 30.

Figure 3:
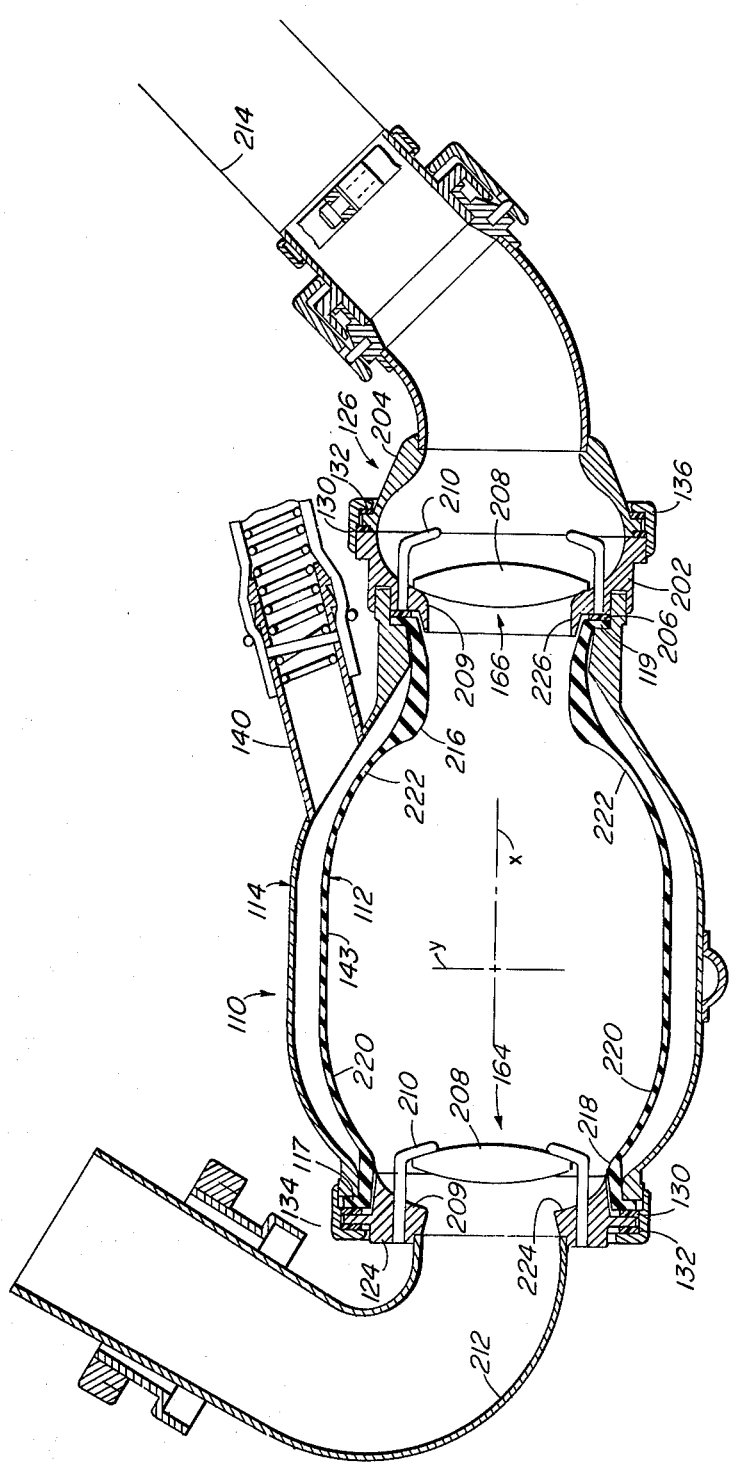
FIG. 3 illustrates an alternate embodiment of the blood pump.

Another embodiment of the blood pump of this invention is illustrated by FIG. 3. Many parts of the device of FIG. 3, though not identical to those in FIGS. 1 and 2, are similar or analogous in structure and function. Parts in FIG. 3 which are similar or analogous to those in FIGS. 1 and 2 have been designated by numbers which are 100 plus numbers used in FIGS. 1 and 2.

The pump 110 includes a flexible bladder 112 mounted within a housing 114 of generally corresponding shape and forming a space between the housing and the bladder. Pneumatic pulses admitted through an inlet 140 produce a three lobe collapse pattern in the bladder 112. The bladder and pump are mounted together at the inlet and outlet ends by adaptor means 124 and 126, together with couplings 134 and 136. At the inlet end the adaptor is mounted between the flange 117 of the bladder 112 and the coupling 134. The coupling 134 is screw-threaded to the housing to apply axial pressure to the adaptor 124 and to form a seal at the inlet of the bladder 112. Contact of the bladder with the housing produces a fluid-tight seal. Pressure applied to the bladder by the adaptor produces a second fluid-tight seal. Between the adaptor and the coupling and also between the adaptor and the bladder are interposed low friction rings 130 and 132 for permitting rotational movement of the adaptor during and after assembly. At the outlet end, the adaptor means 126 appears in two parts, a part 202 adjacent the bladder and a downstream part 204. Parts 202 and 204 are held together by a coupling 136. Part 202 of the adaptor 126 threadedly engages the housing 114 to assist in forming the necessary fluid-tight seals around the flange 117 of the bladder 112. Low friction rings 130 and 132 are interposed, respectively, between the parts 202 and 204 and between the part 204 and the coupling 136. A further low friction ring 206 is provided between the flange 117 and the part 202 to permit assembly of the outlet end of the blood pump 110 without inducing a twist in the bladder.

The pump 110 is provided with an inlet valve means 164 and outlet valve means 166. Each valve means comprises a freely reciprocating valve element 208 held in place by prongs 210. The volumetric flow area through an inlet conduit 212 and an outlet conduit 214 needs to be maintained substantially constant throughout. That is, the annular flow area surrounding valve elements 208 must substantially equal the flow area in conduits 212 and 214. In addition to being configured to provide the necessary flow area, the conduit 224 in the adaptor 124 is configured to form an approximate extension of the contour appearing in the adjacent portions of the bladder 112. Similarly, the inlet end 226 of the part 202 surrounding the outlet valve element 208 acts as a continuation of the small neck of the bladder 112 formed by the portion 216. The bulbous passage formed by parts 202 and 204 permit smooth transition of flow from the valve means 166 to the outlet conduit 214.

As can be appreciated by reference to FIG. 3, the construction described above requires the inlet end of the bladder 112 to be substantially larger in diameter than the outlet end. Thus the bladder 112, unlike the bladder 12 of FIG. 1, is not geometrically symmetrical about any plane perpendicular to the longitudinal axis X. However, it has been discovered that the best and most dependable three lobe collapse pattern is achieved when the bladder 112 is of substantially uniform stiffness about a plane Y perpendicular to the axis X and intersecting the bladder 112 at substantially the midpoint of its enlarged mid-section 143. Symmetry of stiffness of the bladder 112 about the plane Y is approximated by providing a thickened portion 216 adjacent the outlet end of the bladder. The thickened portion is formed in the bladder wall beginning at a point adjacent the outlet end which corresponds approximately to the minimum internal diameter at the inlet end. Progressing from this point toward the outlet opening of the bladder 112, wall thickness increases progressively until the internal diameter of the bladder equals approximately the minimum internal diameter of the outlet conduit 114. Progressing further toward the outlet opening, the wall thickness may be reduced to some extent but it should maintain a sufficient thickness to achieve substantial rigidity compared to mid-section 143 of the bladder. The result is an annular integral ring bulging inward from the wall of the bladder 112 to establish a measure of stiffness. This integral annular ring is characterized by a smooth inner surface to establish desirable flow patterns within the bladder. The inlet end of the bladder 112 may be stiffened slightly to form a rigid sleeve 218 surrounding the adaptor 124. A bladder of substantially uniform stiffness at points equidistant from plane Y results. That is, between a locus at the inlet end designated 220 and a corresponding locus at the outlet end designated 222 there is symmetry of stiffness. The portions of the bladder 112 outside of the space between the zone 220 and 222 possesses substantial stiffness and resists flexure to the extent that the collapse pattern established in the bladder 12 shown in FIG. 1 is substantially approximated, the three lobe collapse occuring between the loci 220 and 222.

The inlet valve means 164 and the outlet valve means 166 operate substantially identically, their differences being such as to adapt them for their location in the overall pump structure. Each valve element 208 is associated with a seat 209. When the area surrounding the bladder 112 is depressurized, arterial pressure present in the outlet conduit 214 is greater than the pressure within the bladder 112 so that the disc 208 of the valve means 166 snaps against its seat 209. Ventricular pressure at the inlet conduit 212, also greater than the pressure within the bladder 212, forces the disc 208 of the inlet valve means 164 away from its seat 209 and against the end of its associated prongs 210. In this manner flow is admitted to the bladder. Upon imposition of a pneumatic pulse to the space between the bladder 112 and the housing 114, the pressure within the bladder exceeds the ventricular pressure. The disc 208 of the pump means 164 snaps against its associated seat 209 to block entry of blood into the bladder 112. Thereafter, as the pressure in the bladder 112 exceeds arterial pressure, the disc 208 of valve means 166 is forced from its seat 209 to a position against the end of the associated prongs 210. As the bladder 112 collapses blood is driven through the valve means 166 to the outlet conduit 214.

As various changes could be made in the above constructions without departing from the scope of the invention, it should be understood that all matter contained in the above description or shown in the accompanying drawings shall be interpreted as illustrative and not in a limiting sense.

I claim:

1. A blood pump comprising:
   a flexible axis-symmetrical bladder having a midsection and end sections, said midsection being of a larger diameter than said end sections;
   said bladder having circular openings, one at each end thereof;
   peripheral means around each of said openings;
   a rigid housing enclosing said bladder;
   means in said housing forming an opening coinciding with each of said bladder openings for sealing engagement with each said peripheral means;
   means forming a third opening in said housing for introducing compressed gas between said bladder and said housing;
   a pair of end adaptor means having passageways for conducting blood to and from said bladder, one said adaptor means being located at each of said bladder openings for sealing engagement with the associated peripheral means;
   means for holding each said adaptor means in sealing engagement with the corresponding said peripheral means and each said peripheral means in sealing engagement with said housing; and
   a pair of rings having a substantially lower coefficient of friction than either said adaptor or said peripheral means, one ring being interposed between each said adaptor means and its associated peripheral means for substantially reducing transmission of rotational forces between said adaptor means and said peripheral means.

2. The blood pump of claim 1 wherein:
   each said adaptor means defines an annular surface external to said bladder and facing away from said bladder; and
   said holding means comprises a pair of couplings removably affixed to said housing each being engageable with one of said annular surfaces.

3. The blood pump of claim 2 further comprising a second pair of rings having a substantially lower coefficient of friction than either said couplings or said annular surfaces, one ring being interposed between each said coupling and the corresponding annular surface.

4. A blood pump comprising:
   a flexible axis-symmetrical bladder;
   said bladder having circular openings of substantially equal size, one at each end thereof, said openings being oriented perpendicularly to the axis of said bladder;
   circumferential flange means around each of said openings;
   a rigid housing enclosing said bladder;
   means in said housing forming an opening coinciding with each of said bladder openings for sealingly engaging each said flange means around the entire circumference thereof;
   means forming a third opening in said housing for introducing compressed gas between said bladder and said housing;
   a pair of circular end adaptors having passageways for conducting blood to and from said bladder, one adaptor being located at each of said bladder openings and forming means for mating with said flange means around the entire circumference thereof;
   a pair of rings, one interposed between each said adaptor and said flange means for sealing engagement with said adaptor and flange means, said rings having a substantially lower coefficient of friction than said adaptor or said flange means; and
   means for holding each of said adaptors in sealing relationship with the corresponding flange means and each said flange means in sealing engagement with said housing.

5. The blood pump of claim 4 wherein:
   each said adaptor defines an annular surface external to said bladder and facing away from said bladder; and
   said holding means comprises a pair of couplings removably affixed to said housing, each being engageable with one of said annular surfaces.

6. The blood pump of claim 5 further comprising a second pair of rings having a substantially lower coefficient of friction than either said couplings or said annular surfaces, one ring being interposed between each said coupling and the corresponding annular surface.

7. A blood pump comprising:
   a flexible axis-symmetrical bladder having a midsection, a first end section defining a first port and a second end section defining a second port smaller in diameter than said first port;
   means associated with said bladder for producing substantially equal stiffness at all points on said bladder equidistant from a plane perpendicular to its axis of symmetry and located substantially at the center of said midsection, for maximizing collapse during external pressurization, said means for producing having at least an annular stiffening means associated with the wall of said second end section;
   peripheral means around each of said first and second ports;
   a rigid housing enclosing said bladder;

means in said housing forming an opening coinciding with each of said first and second ports for sealing engagement with each said peripheral means;

means forming a third opening in said housing for introducing compressed gas between said bladder and said housing;

a pair of end adaptor means having passageways for conducting blood to and from said bladder, one adaptor means being located at each of said first and second ports for sealing engagement with the associated peripheral means; and means for holding each said adaptor means in sealing engagement with the corresponding said peripheral means and each said peripheral means in sealing engagement with said housing.

8. The blood pump of claim 7, wherein said means forming said annular stiffening portion comprises a thickened annular portion of the wall of said bladder.

* * * * *